United States Patent [19]

Halka

[11] Patent Number: Plant 7,554

[45] Date of Patent: Jun. 11, 1991

[54] PAGODATREE 'HALKA'

[75] Inventor: Chester J. Halka, Englishtown, N.J.

[73] Assignee: J. Frank Schmidt & Son Co., Boring, Oreg.

[21] Appl. No.: 427,304

[22] Filed: Oct. 26, 1989

[51] Int. Cl.[5] ..... A01H 5/00

[52] U.S. Cl. ..... Plt./51

[58] Field of Search ..... Plt./51

[56] References Cited

U.S. PATENT DOCUMENTS

P.P. 2,338 1/1964 Flemer, III ..... Plt. 51

P.P. 5,524 7/1985 Flemer, III ..... Plt. 51

OTHER PUBLICATIONS

Bailey, 1935, "The Standard Cyclopedia of Horticulture", The MacMillan Company, New York, pp. 3191-3192.

*Primary Examiner*—Howard J. Locker

*Attorney, Agent, or Firm*—Klarquist, Sparkman, Campbell, Leigh & Whinston

[57] ABSTRACT

A novel Japanese pagodatree characterized by a high percentage of branches on two year old trees of a desired caliper, a growth rate and foliage size between that of seedling and Regent pagodatrees, leaflets with a high length to width ratio, numerous small lenticels, and leaves with heavily pubescent undersides.

1 Drawing Sheet

The present invention relates to a new and distinct variety of Japanese pagodatree of the species botanically known as *Sophora japonica*. I have named my new variety "Halka". I discovered my new variety as a chance seedling of unknown parentage which was being grown in a cultivated area of my nursery in Englishtown, N.J.

While caring for this nursery, my attention was first drawn to the plant by its bright green foliage, dense growth, and rounded canopy. Other seedling pagodatrees in my nursery tended to have a loose, open growth habit and less attractive foliage.

Close observations of the new seedling and continued observations of progeny thereof subsequently asexually propagated under my direction by budding on seedling pagodatree understock, has confirmed that the unique characteristics of my new variety are a result of a seedling variation. I am therefore convinced that my new tree represents a new and improved variety of *Sophora japonica*, as particularly evidenced by the following unique combination of characteristics, which have proven firmly fixed, are outstanding therein, and which distinguish my new variety from other varieties of this species:

1. A dense, rounded crown with up-sweeping branches;

2. Foliage which is pinnately compound, with large, glossy leaflets, the leaflets being pubescent on the underside;

3. A growth rate which is higher than pagodatree seedlings and lower than the Regent variety of pagodatree, this latter variety often being considered to grow too fast for proper management in a nursery;

4. Leaves and leaflet size which are both longer and wider than leaves and leaflets of seedling pagodatrees but smaller in both dimensions than leaves and leaflets of the Regent variety of pagodatree;

5. Leaflets having a length to width ratio which is higher than the ratio of seedling or Regent varieties of pagodatrees;

6. Extremely small, numerous lenticles which dot the stems; and

7. An extremely large percentage of branches in two year old trees which are of a caliper which contributes to a better form of pagodatree.

The accompanying photographs depict the color of the foliage of my new variety as nearly true as is resonably possible to make the same in a color illustration of this character.

FIG. 1 is a color photograph of a two year old tree of the present invention;

FIG. 2 is a color photograph of leaves of the tree of the present invention;

FIG. 3 is a color photograph of a trunk of the tree of the present invention showing the numerous small lenticels thereon; and FIG. 4 is a color photograph of the underside of a leaflet from a tree of the present invention showing its pubescence.

The growth rate of my new variety of tree has proven to be greater than that of seedling pagodatrees, but less than that for the Regent pagodatree variety. As previously mentioned, Regent pagodatrees suffer from the drawback of growing too fast for proper management in a nursery in the view of many nurserymen. In addition, the leaves and leaflets of my new variety are both longer and wider than the leaves and leaflets of the seedling variety of pagodatrees, but smaller in both dimensions than the leaves and leaflets of the Regent variety of pagodatree. Moreover, the length to width ratio of the leaflets of my tree have proven to be higher than that of either the seedling pagodatrees or Regent pagodatree variety. Also, my tree has extremely small, numerous lenticels which dot the stem or trunk. Observations of the lenticels of my new variety have confirmed them to be much more numerous than those of the seedling and Regent pagodatree varieties, although the differences between my new variety and the seedling variety are not as great as the differences between my new variety and the Regent variety.

Table I, below, sets forth a comparison of characteristics of my new variety of pagodatree to the corresponding characteristics of seedling pagodatrees and Regent variety pagodatrees. To obtain the leaf measurements, observations were made of ten leaves from each variety with the measurements being averaged. In addition, ten trees of each variety were compared to confirm the observations concerning lenticels of the varieties. Of course, it is always possible for an individual leaf or leaflet or a tree to deviate from these averages, but these observations do confirm the distinctive nature of my new variety of pagodatree.

TABLE I

| | Comparison of Growth Rate Leaf & Leaflet Sizes and Lenticels | | |
|---|---|---|---|
| | New Variety | Seedling | Regent |
| 1 yr. tree height | 2.45 m | 1.79 m | 2.75 m |
| 1 yr. caliper at base | 1.98 cm | 1.19 cm | 2.21 cm |
| Leaf Length | 23.4 cm | 20.6 cm | 26.8 cm |
| Leaf Width | 13.2 cm | 8.3 cm | 14.9 cm |
| Leaflet Length | 6.5 cm | 3.9 cm | 7.45 cm |
| Leaflet width | 2.77 cm | 1.93 cm | 3.79 cm |
| Leaflet Length /Width ratio | 2.34 | 2.02 | 1.96 |
| Lenticels per inch, measurements taken 36" below 1 yr. tree top | 18.9 | 14.3 | 9.9 |
| Lenticel size, shape | 1–2 mm, rounded to oval | ½–1 mm, oval | 2–8 mm, rounded to oval |

In addition, an analysis of the branching characteristics of two year old trees of my new variety showed them to be of a better form than seedling pagodatrees or Regent pagodatrees. Two year old branch trees of my new variety have a quite uniform branch angle of 45 to 60 degrees while two year old *Sophora japonica* 'Regent' trees have been observed to have branch angles of from 30 to 90 degrees. Ideal branches on a two year old pagodatree are generally between ¼ inch and ½ inch in thickness at the base. Smaller branches tend to be too weak while heavier branches tend to become too dominant, competing with the central leader of a tree and interfering with the symmetry of the tree. This difference may explain why pagodatrees of my new variety appear to grow straighter than the Regent pagodatrees. Table II, below, compares the distribution of branches of various sizes of two year old trees of my new variety of pagodatree, seedling pagodatrees, and Regent variety pagodatree. The branches of ten trees of each type were compared to determine this distribution.

TABLE II

| | Branch Size Distribution on Two Year Old Trees | | |
|---|---|---|---|
| Caliper | New Variety | Seedling | Regent |
| 0–¼" | 13% | 53% | 24% |
| ¼"–⅜" | 31% | 32% | 27% |
| ⅜"–½" | 56% | 15% | 29% |
| ½"–1" | 0% | 0% | 20% |

In generating Tables I and II, a comparison was made of tree of the specified varieties growing in the J. Frank Schmidt & Son Co. nursery in Independence, Oreg.

The underside of the leaflets of my new variety vary from moderately to heavily pubescent. In comparison, the underside of the leaflets on seedling pagodatrees of the species vary from sparsely appressed pubescent to nearly glabrous.

Otherwise, so far as I have observed at this time, my new variety of pagodatree is generally typical of the species.

The following is a detailed description of my new variety of *Sophora japonica* tree, with color terminology in accordance with The Royal Horticultural Society colour chart (hereinafter R.H.S.), published by The Royal Horticultural Society of London.

Parentage: A chance seedling of unknown parentage.

Propagation: Holds to distinguishing characteristics through succeeding propagation by budding.

Localities where grown and observed: Englishtown, N.J. and Independence, Oreg.

Tree: Dense, rounded crown with up-sweeping branches.

Growth rate: Relatively fast growth rate which is greater than that of seedling pagodatrees but which is slower than that of Regent pagodatrees grown under comparable conditions in a nursery.

Bark color: One and two-year old stems are green (like R.H.S. 137a to 139a). By the fifth year they are grayed-green (similar to R.H.S. 194a).

Branch angle: Two-year old branch trees have a quite uniform branch angle of about between 45°–60°.

Foliage:

*Leaves.*—Pinnately compound, with large glossy leaflets, moderately to heavily pubescent on the underside.

*Leaf size.*—Length — typically about 23.4 cm; Breadth typically about 13.2 cm; (dimensions are averages of measurements taken from 10 leaves).

*Leaflet size.*—Length — typically about 6.5 cm; Breadth typically about 2.8 cm (dimensions are averages of measurements taken from 10 leaves).

*Leaflet shape.*—Ovate to oblong ovate.

*Leaflet margin.*—Entire.

*Leaflet tip.*—Acute.

*Leaflet base.*—Rounded.

*Number of leaflets.*—13 to 15.

*Branches and Trunk.*—Numerous small lenticels of rounded to oval shape lenticel color: Orange-white (similar to R.H.S. 159a to 159b).

*Color.*—The leaf summer color is a yellow-green (similar to R.H.S. 147a). In the fall, the leaves turn to a yellow color (similar to R.H.S. 11a.).

I claim:

1. A new and distinct variety of Japanese pagodatree, substantially as herein shown and described, characterized particularly as to novelty by a high percentage of branches on two year old trees of a desired caliper, a growth rate and foliage size between that of seedling and the Regent pagodatree variety, leaflets with a length to width ratio higher than that of seedling and Regent pagodatrees, numerous small lenticels, and leaves with heavily pubescent undersides.

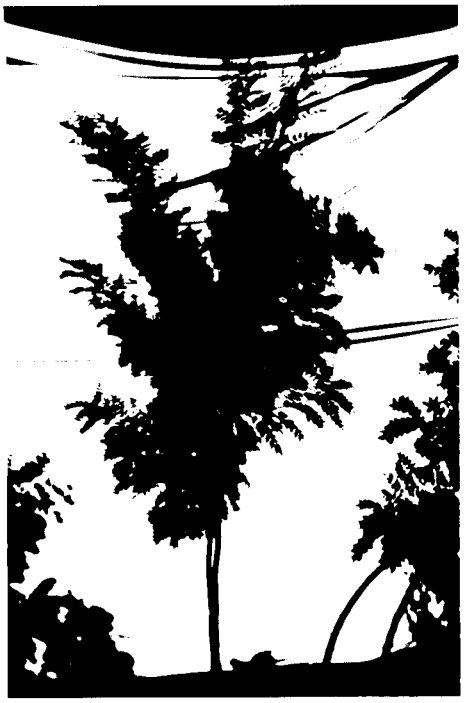
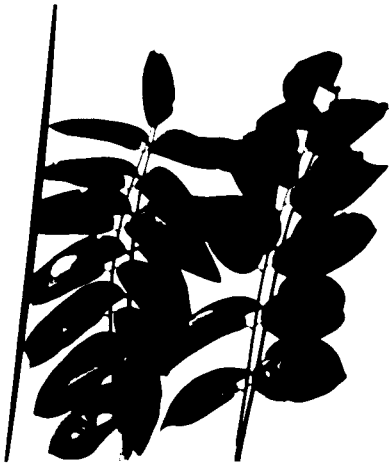
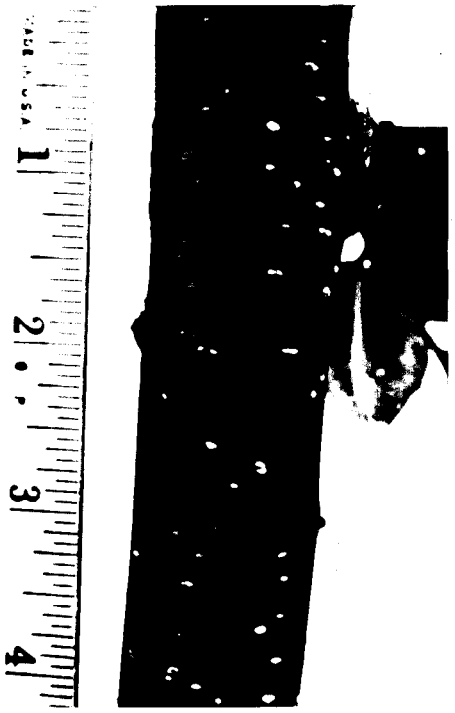
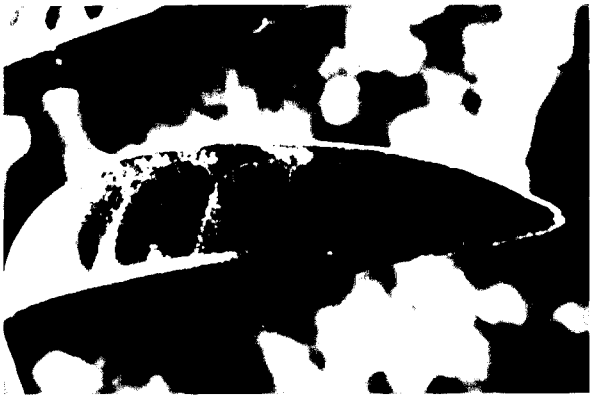

* * * * *